United States Patent [19]
Konishi et al.

[11] Patent Number: 5,773,449
[45] Date of Patent: Jun. 30, 1998

[54] THIOQUINOLONE COMPOUNDS WHICH HAVE USEFUL PHARMACEUTICAL ACTIVITY

[75] Inventors: Masataka Konishi; Naoki Fukuda; Yukio Oku; Hiroaki Yamazaki; Kazuhiro Imaizumi; Hideshi Kobayashi, all of Ohizumi-machi, Japan

[73] Assignee: Zenyaku Kogyo Kabushiki Kaisha, Tokyo, Japan

[21] Appl. No.: 809,722

[22] PCT Filed: Oct. 6, 1995

[86] PCT No.: PCT/JP95/02052

§ 371 Date: Apr. 7, 1997

§ 102(e) Date: Apr. 7, 1997

[87] PCT Pub. No.: WO96/11187

PCT Pub. Date: Apr. 18, 1996

[30] Foreign Application Priority Data

Oct. 7, 1994 [JP] Japan ................................. 6-244348

[51] Int. Cl.$^6$ ............... C07D 215/36; A61K 31/47
[52] U.S. Cl. ............ 514/312; 514/291; 546/153; 546/156; 546/89
[58] Field of Search .................. 546/153, 156, 546/89; 514/312, 291

[56] References Cited

U.S. PATENT DOCUMENTS

| | | | |
|---|---|---|---|
| 4,619,994 | 10/1986 | Shortridge | 534/738 |
| 5,081,121 | 1/1992 | Osawa et al. | 514/312 |
| 5,189,210 | 2/1993 | Wright et al. | 562/418 |

FOREIGN PATENT DOCUMENTS 0061461  3/1989  Japan ................... 546/153

*Primary Examiner*—Zinna Northington Davis
*Attorney, Agent, or Firm*—Oblon, Spivak, McClelland, Maier & Neustadt, P.C.

[57] ABSTRACT

Disclosed is a thioquinolone derivative which exhibits highly selective antibacterial activity against *Helicobacter pylori*.

20 Claims, No Drawings

THIOQUINOLONE COMPOUNDS WHICH HAVE USEFUL PHARMACEUTICAL ACTIVITY

This is a 371 application of PCT/JP95102052 filed on Oct. 6, 1995.

TECHNICAL FIELD

The present invention relates to novel thioquinolone derivatives represented by the formula I and having antibacterial activity against *Helicobacter pylori* or pharmaceutically acceptable salts thereof and antibacterial agents containing the derivatives as effective components:

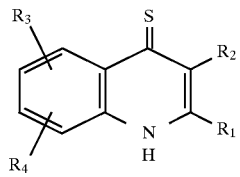

wherein $R_1$ and $R_2$ respectively represent hydrogen atom or $R_1$ and $R_2$ are joined to form $-O-(CH_2)_2-$;

$R_3$ represents halogen atom, $C_1-C_{12}$ alkyl group, $C_1-C_{12}$ alkoxy group, lower alkylsulfonyloxy group, carboxy lower alkoxy group, lower alkylthio group, benzyloxy group, benzylthio group, phenoxy group, styryl group, nitro group, phenyl group, naphthyl group, piperazinyl group, morpholino group or hydroxyl group or represents $-CH_2R_5$, $-COR_6$ or $-NR_7R_8$ wherein $R_5$ represents benzyl group, phenyl group, hydroxyl group, lower alkoxy group, lower alkylcarbonyloxy group, phenoxy group, di-lower alkylamino group or benzimidazolylthio group, $R_6$ represents lower alkyl group or amino group and $R_7$ and $R_8$ respectively represent lower alkyl group; and $R_4$ represents hydrogen atom or lower alkyl group or is coupled with $R_3$ to form cyclohexene ring, benzene ring or pyridine ring, $R_3$ being not halogen atom at any of positions 5 to 8, methyl group at position 6 or methoxy group at position 6 of the quinoline ring when $R_1$, $R_2$ and $R_4$ are respectively hydrogen atom, $R_3$ and $R_4$ being not at positions 6 and 7 or positions 6 and 8 of the quinoline ring when $R_1$ and $R_2$ are respectively hydrogen atom and $R_4$ is lower alkyl group.

BACKGROUND ART

*Helicobacter pylori* is a spiral, short rod-shaped, gram-negative bacterium having at its one pole several sheath flagella. The bacteria are detected both in the gastric mucous layer and on the surface of gastric epithelial cells.

The fact that spiral bacteria live on and in a gastric mucosa has been observed by many researchers. Firstly in 1983, Marshall et al. succeeded in cultivating spiral bacteria through isolation of the same from a gastric mucosa. The bacterium was originally named *Campylobacter pylori* since its shapes and biochemical characteristics are analogous to those of the genus Campylobacter which is one of known enteritis-causing bacterial genera. However, later bacterial taxonomic researches established a new independent genus including the bacterium, and the bacterium was renamed *Helicobacter pylori*.

In 1984, Marshall et al. detected the bacteria at high percentage from patients suffering from peptic ulcer such as gastric and duodenal ulcers and chronic gastritis, and suggested relevance of the bacteria to occurrence and reccurrence of these diseases. As conventional remedies against peptic ulcer, medical treatments with gastric secretion inhibitors have been utilized; advent of $H_2$-blocker such as cimetidine and proton-pump inhibitor such as omeprazole enhanced the cure rate up to 80–90%. However, it has been reported that about 50% of patients healed with administration of anti-ulcer agents have relapse or reccurrence of ulcers within twelve months and that, particularly, patients healed with gastric secretion inhibitors such as $H_2$-blockers and proton-pump inhibitors have relapse rate of as high as 70–90%. Thus, prevention of the relapse or reccurrence is one of greatest problems in the treatment.

There have, however, been recently increasingly reported that removal of *Helicobacter pylori* (hereinafter referred to as Hp) with an antibacterial agent will decrease ulcer relapse rate [see for example SAISHIN-IGAKU: Vol. 44, No. 2, pp. 295–302, (1989)]; and, in February 1994, NIH in U.S.A. advised necessity of eradicating Hp in the treatment of peptic ulcer. Hp-removing agents used nowadays are for example antibiotics and bismuth preparations. Antibiotics are not suitable for long-term use since they may also affect other intestinal bacteria and may cause advent of resistant bacteria. Treatment with bismuth preparations is rather problematic since the bismuth preparations are weak in antibacterial activity and may cause vomiting, diarrhea and/or side effects on central nervous system.

Anti-ulcer agents with antibacterial activities against Hp have been proposed for example in Japanese Patent Provisional Publication (Kokai) No. 4-364160 (European Patent Provisional Publication No. 470006) and Japanese Patent Provisional Publication (Kokai) No. 5-117268; however, none of the proposed agents have sufficient selectivity and antibacterial activity. Under such circumstances, there have been demand on development of preparations having higher selectivity on Hp as well as antibacterial activity against Hp in the treatment of peptic ulcer and chronic gastritis with Hp infection.

In order to overcome the above-mentioned problems, we, the inventors carried out intensive studies to find that a thioquinolone derivative of the formula I has excellent selective antibacterial activity against Hp, thus accomplishing the present invention.

Conventionally proposed thioquinolone derivatives are for use as synthetic intermediates in agricultural and horticultural bactericides, cardiotonic agents or the like [see Japanese Patent Provisional Publication (Kokai) No. 6-41117 and U.S. Pat. No. 5,081,121]. The present invention is a first proposal on thioquinolone derivatives as antibacterial agents against Hp.

DISCLOSURE OF THE INVENTION

The terms used for definition of letters in the formula I by which the compounds of the present invention are represented are defined and exemplified in the following.

The wording "lower" refers to a group having 1 to 6 carbon atoms unless otherwise indicated.

The "lower alkyl group" refers to a straight- or branched-chain alkyl group such as methyl, ethyl, n-propyl, isopropyl, n-butyl, tert-butyl, n-pentyl, n-hexyl or the like.

The "lower alkoxy group" refers to a straight- or branched-chain alkoxy group such as methoxy, ethoxy, n-propoxy, isopropoxy, n-butoxy, tert-butoxy, n-pentyloxy, n-hexyloxy or the like.

The wording "$C_1-C_{12}$" refers to a group having 1 to 12 carbon atoms.

The "$C_1$–$C_{12}$ alkyl group" refers to a straight- or branched-chain alkyl group such as heptyl, octyl, nonyl, decyl, undecyl, dodecyl in addition to the above-mentioned groups as "lower alkyl group".

The "$C_1$–$C_{12}$ alkoxy group" refers to a straight- or branched-chain alkoxy group such as heptyloxy, octyloxy, nonyloxy, decyloxy, undecyloxy, dodecyloxy in addition to the above-mentioned groups as "lower alkoxy group".

The "halogen atom" may be fluorine, chlorine, bromine or iodine atom.

The compounds according to the present invention may be as follows, though the present invention is not limited to these compounds.

5-Methylquinoline-4(1H)-thione
7-Methylquinoline-4(1H)-thione
8-Methylquinoline-4(1H)-thione
8-Isopropylquinoline-4(1H)-thione
7,8-Dimethylquinoline-4(1H)-thione
7-Isopropylquinoline-4(1H)-thione
7-n-Hexylquinoline-4(1H)-thione
7-Dodecylquinoline-4(1H)-thione
7-Hydroxymethylquinoline-4(1H)-thione
7-Methoxymethylquinoline-4(1H)-thione
7-Phenoxymethylquinoline-4(1H)-thione
7-Acetoxymethylquinoline-4(1H)-thione
7-Styrylquinoline-4(1H)-thione
7-Benzylquinoline-4(1H)-thione
7-Phenethylquinoline-4(1H)-thione
7-N,N-Dimethylaminomethylquinoline-4(1H)-thione
7-(2-Benzimidazolyl)thiomethylquinoline-4(1H)-thione
7-Phenylquinoline-4(1H)-thione
7-(2-Naphtyl)quinoline-4(1H)-thione
7-Hydroxyquinoline-4(1H)-thione
7-Methoxyquinoline-4(1H)-thione
8-Methoxyquinoline-4(1H)-thione
7-Ethoxyquinoline-4(1H)-thione
7-n-Propoxyquinoline-4(1H)-thione
7-Isopropoxyquinoline-4(1H)-thione
8-Isopropoxyquinoline-4(1H)-thione
7-tert-Butoxyquinoline-4(1H)-thione
7-n-Hexyloxyquinoline-4(1H)-thione
7-Octyloxyquinoline-4(1H)-thione
7-Dodecyloxyquinoline-4(1H)-thione
7-Benzyloxyquinoline-4(1H)-thione
7-Phenoxyquinoline-4(1H)-thione
7-(5-Carboxy-n-pentyloxy)quinoline-4(1H)-thione
7-Methanesulfonyloxyquinoline-4(1H)-thione
7-Methylthioquinoline-4(1H)-thione
7-Isopropylthioquinoline-4(1H)-thione
7-n-Butylthioquinoline-4(1H)-thione
7-Benzylthioquinoline-4(1H)-thione
7-Acetylquinoline-4(1H)-thione
7-Carbamoylquinoline-4(1H)-thione
7-N,N-Dimethylaminoquinoline-4(1H)-thione
7-N,N-Diethylaminoquinoline-4(1H)-thione
8-N,N-Dimethylaminoquinoline-4(1H)-thione
7-(N-Isopropyl-N-methylamino)quinoline-4(1H)-thione
7-(1-Piperazinyl)quinoline-4(1H)-thione
7-Morpholinoquinoline-4(1H)-thione
7-Nitroquinoline-4(1H)-thione
8-Nitroquinoline-4(1H)-thione
7-Chloro-2,3-dihydrofuro[2,3-b]quinoline-4(1H)-thione
7-Chloro-8-methylquinoline-4(1H)-thione
7-Isopropyl-8-chloroquinoline-4(1H)-thione
7-N,N-Dimethylamino-8-ethylquinoline-4(1H)-thione
7-Methyl-8-methoxyquinoline-4(1H)-thione
5-Nitro-8-methylquinoline-4(1H)-thione
7-Isopropyl-8-N,N-dimethylaminoquinoline-4(1H)-thione
Benzo[h]quinoline-4(1H)-thione
7,8,9,10-Tetrahydrobenzo[h]quinoline-4(1H)-thione
1,7-Phenanthroline-4(1H)-thione
1,10-Phenanthroline-4(1H)-thione The compounds of the present invention may exist in the form of tautomers as shown below. It is, therefore, to be understood that any of such tautomers are included in the category of the compounds of the formula I.

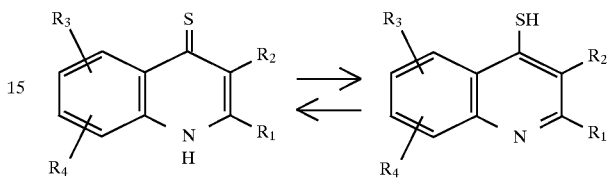

wherein $R_1$, $R_2$, $R_3$ and $R_4$ are as defined above.

Furthermore, according to substituents and the like, the compounds of the present invention may be in the form of pharmaceutically acceptable salts such as alkali salts, organic ammonium salts or acid addition salts. The appropriate alkali salts which can be used include, for example, potassium salt, sodium salt, calcium salt, magnesium salt and barium salt. The appropriate organic ammonium salts which can be used include, for example, ethyl ammonium salt and trimethyl ammonium salt. And, the appropriate acid addition salts which can be used include inorganic salts such as hydrochloride, sulfate, hydrobromide, nitrate and phosphate as well as organic acid salts such as acetate, oxalate, propionate, glycolate, lactate, pyruvate, malonate, succinate, maleate, fumarate, malate, tartarate, citrate, benzoate, cinnamate, methanesulfonate, benzenesulfonate, p-toluenesulfonate salicylate.

The compounds of the present invention may be prepared by the following procedure of conversion of 4-hydroxyquinoline derivative (formula II) or 4-haloquinoline derivative (formula III) to thione at the position 4 of the quinoline ring as shown in the following reaction scheme 1 or 2. (1) In conversion of 4-hydroxyquinoline derivative of the formula II to thione, a mole of compound of the formula II in a solvent such as pyridine, toluene or xylene is reacted with a mole or more of phosphorus pentasulfide, silicon disulfide or Lawesson's reagent for 0.5–5 hours under reflux to obtain the compound of the present invention.

Reaction Scheme 1

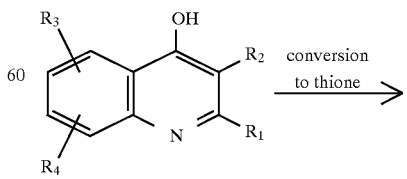

Formula II

-continued
Reaction Scheme 1

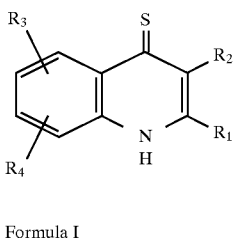

Formula I wherein $R_1$, $R_2$, $R_3$ and $R_4$ are as defined above. (2) In conversion of 4-haloquinoline derivative of the formula III to thione, a mole of compound of the formula III in a solvent such as methanol, ethanol, n-propanol is reacted with a mole or more of sodium hydrosulfide, potassium hydrosulfide or thiourea at room temperature for 8 hours to 8 days or at 60°–100° C. for 0.5–48 hours to obtain the compound of the present invention.

Reaction Scheme 2

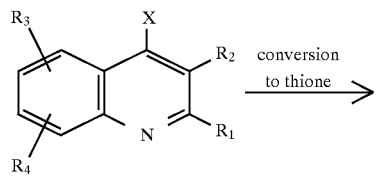

Formula III conversion to thione

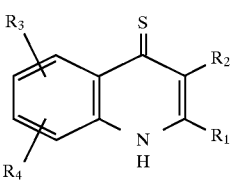

Formula I wherein $R_1$, $R_2$, $R_3$ and $R_4$ are as defined above and X represents halogen atom.

The compounds of the present invention thus obtained may be separated and purified by a usual manner such as extraction, condensation, neutralization, filtration, recrystallization or column chromatography, if necessary.

The pharmaceutically acceptable salts of the compounds of the present invention may be prepared by various known methods in the art.

The compounds of the formulas II and III which are the starting materials in the above-mentioned processes can be readily synthesized according to a process described for example in Org. Syn. Coll. Vol. 3, p. 272 or Japanese Patent Publication (Kokoku) No. 47-43952.

Next, described is antibacterial activity of the compound of the present invention represented by the formula I. The numbers of test compounds in Antibacterial Tests 1 and 2 correspond to those in Examples referred to hereinafter. Controls used were antibiotic (amoxicillin) and anti-ulcer agent (lansoprazole) having antibacterial activity against Hp.

Antibacterial test 1

Antibacterial test against Hp was performed in substantial accordance with agar plate dilution method (anaerobic MIC method) based on Standard method of The Japan Society of Chemotherapy to determine minimum inhibitory concentration (MIC) of the respective test compounds.

[Preparation of medium for sensitivity testing]

The respective test compounds were sequentially dissolved in dimethyl sulfoxide (DMSO) and serially diluted twofold. These diluted solutions of the compounds are respectively added to brucella agar medium (prepared by Difco) containing 7% horse blood free from fibrin (prepared by NIPPON BIOTEST KENKYUSHO) to prepare agar plates for determination with concentration of 0.05–100 μg/ml.

[Preparation of inocula]

Strain used for inoculation was *Helicobacter pylori* standard strain ATCC 43526 (NCTC 11916). For pre-culturing of bacteria to be inoculated, the above-mentioned strain freezingly conserved at −135° C. was thawed in a warm bath (40° C.), applied on a brucella agar medium containing 7% horse blood free from fibrin, and microaerobically cultured in a jar for anaerobic bacteria at 37° C. for 3 days. The solution of bacteria to be inoculated was prepared by collecting colonies grown on the culture medium and suspending the same in the brucella broth.

The suspension was made such that the concentration of the bacteria to be inoculated provides adsorbancy $O.D_{570nm}=0.50$, and $2.0\times10^7$ CFU/ml of the solution of the bacteria was prepared, 5 μl of which was inoculated with multi-inoculator (manufactured by SAKUMA SEISAKUSHO). Culturing was performed for 3 days under the same conditions as those of the pre-culturing and the MIC (unit: μg/ml) was determined by observing whether the bacteria grew or not. The obtained results are shown in Table 1.

TABLE 1

| test compound | MIC (μg/ml) |
|---|---|
| compound 1 | 0.39 |
| compound 2 | 1.56 |
| compound 3 | 1.56 |
| compound 6 | 1.56 |
| compound 7 | 6.25 |
| compound 11 | 0.39 |
| compound 12 | 6.25 |
| compound 13 | 1.56 |
| compound 15 | 0.39 |
| compound 16 | 1.56 |
| compound 17 | 0.39 |
| compound 19 | 3.13 |
| compound 22 | 3.13 |
| compound 23 | 0.78 |
| compound 24 | 1.56 |
| compound 25 | 6.25 |
| compound 26 | 1.56 |
| compound 28 | 0.39 |
| compound 29 | 0.78 |
| compound 30 | 1.56 |
| compound 31 | 0.39 |
| compound 32 | 0.78 |
| compound 33 | 6.25 |
| compound 34 | 0.78 |
| compound 36 | 0.39 |
| compound 37 | 0.78 |
| compound 38 | 0.78 |
| compound 39 | 0.39 |
| compound 40 | 0.20 |
| compound 41 | 0.78 |
| compound 42 | 0.39 |
| compound 45 | 0.39 |
| compound 46 | 3.13 |
| compound 47 | 0.20 |
| compound 48 | 0.20 |

TABLE 1-continued

| test compound | MIC (μg/ml) |
|---|---|
| compound 49 | 0.39 |
| compound 50 | 1.56 |
| compound 51 | 1.56 |
| compound 52 | 6.25 |
| compound 53 | 3.13 |
| compound 54 | 3.13 |
| compound 55 | 0.39 |
| amoxicillin | 0.05 |
| lansoprazole | 12.5 |

As is clear from the above table 1, the compounds of the present invention exhibit excellent antibacterial activities against Hp. Structurally, the compounds of the formula I wherein $R_1$, $R_2$ and $R_4$ are respectively hydrogen atom and $R_3$ is at position 7 or 8 of the quinoline ring or wherein $R_1$ and $R_2$ are respectively hydrogen atom and $R_3$ and $R_4$ are at the positions 7 and 8 of the quinoline ring exhibited especially excellent activities.

Antibacterial Test 2

Then, tested were antibacterial activities of the typical compounds of the present invention against gram-positive and-negative bacteria other than Hp. MICs of the typical compounds of the present invention were determined in substantial accordance with agar plate dilution method (aerobic MIC method) based on Standard method of The Japan Society of Chemotherapy.

[Preparation of medium for sensitivity testing]

The respective test compound were dissolved in dimethyl sulfoxide (DMSO) and serially diluted twofold. These diluted solutions of the compounds were respectively added to sensitive-disk agar medium-N (manufactured by NISSUI SEIYAKU) to prepare agar plates for determination with concentration of 0.05–100 μg/ml.

[Preparation of inocula]

Strains used for inoculation were 7 species as shown in Table 2. The below-mentioned strains freezingly conserved at −135° C. were thawed in a warm bath (40° C.), cultured in a sensitivity-determining bouillon at 37° C. for 18–20 hours, and then diluted with the above-mentioned medium to prepare about 1.0×10⁶CFU/ml of bacterial solution.

Inoculation was made by 5 μl by multi-inoculator (manufactured by SAKUMA SEISAKUSHO). Culturing was made under the same conditions as those of the pre-culturing and the MIC (unit: μg/ml) was determined by observing whether the bacteria grew or not. The obtained results are shown in Tables 2 to 12.

TABLE 2

| | MIC (μg/ml) | | |
|---|---|---|---|
| strain | compound 1 | Compound 2 | compound 3 |
| S.aureus FDA 209P | 50 | >100 | >100 |
| M.luteus ATCC 9341 | >100 | >100 | >100 |
| E.faecalis RIMD 3336001 | >100 | >100 | >100 |
| B.subtilis PCI 219 | >100 | >100 | >100 |
| E.coli NIHJ JC-2 | >100 | >100 | >100 |
| K.pneumoniae PCI 602 | >100 | >100 | >100 |
| P.aeruginosa IFO 3445 | >100 | >100 | >100 |

TABLE 3

| | MIC (μg/ml) | | |
|---|---|---|---|
| strain | compound 6 | compound 15 | compound 16 |
| S.aureus FDA 209P | >100 | >100 | 50 |
| M.luteus ATCC 9341 | >100 | >100 | 100 |
| E.faecalis RIMD 3336001 | >100 | >100 | 50 |
| B.subtilis PCI 219 | >100 | >100 | 100 |
| E.coli NIHJ JC-2 | >100 | >100 | >100 |
| K.pneumoniae PCI 602 | >100 | >100 | >100 |
| P.aeruginosa IFO 3445 | >100 | >100 | >100 |

TABLE 4

| | MIC (μg/ml) | | |
|---|---|---|---|
| strain | compound 17 | compound 22 | compound 23 |
| S.aureus FDA 209P | >100 | >100 | >100 |
| M.luteus ATCC 9341 | >100 | >100 | >100 |
| E.faecalis RIMD 3336001 | >100 | >100 | >100 |
| B.subtilis PCI 219 | >100 | >100 | >100 |
| E.coli NIHJ JC-2 | >100 | >100 | >100 |
| K.pneumoniae PCI 602 | >100 | >100 | >100 |
| P.aeruginosa IFO 3445 | >100 | >100 | >100 |

TABLE 5

| | MIC (μg/ml) | | |
|---|---|---|---|
| strain | compound 24 | compound 26 | compound 28 |
| S.aureus FDA 209P | >100 | 100 | 25 |
| M.luteus ATCC 9341 | >100 | >100 | 50 |
| E.faecalis RIMD 3336001 | >100 | >100 | 50 |
| B.subtilis PCI 219 | >100 | >100 | >100 |
| E.coli NIHJ JC-2 | >100 | >100 | >100 |
| K.pneumoniae PCI 602 | >100 | >100 | >100 |
| P.aeruginosa IFO 3445 | >100 | >100 | >100 |

TABLE 6

| | MIC (μg/ml) | | |
|---|---|---|---|
| strain | compound 29 | compound 30 | compound 31 |
| S.aureus FDA 209P | 25 | >100 | >100 |
| M.luteus ATCC 9341 | 50 | 100 | >100 |
| E.faecalis RIMD 3336001 | 50 | >100 | >100 |
| B.subtilis PCI 219 | 100 | >100 | >100 |
| E.coli NIHJ JC-2 | >100 | >100 | >100 |
| K.pneumoniae PCI 602 | >100 | >100 | >100 |
| P.aeruginosa IFO 3445 | >100 | >100 | >100 |

TABLE 7

| strain | MIC (µg/ml) | | |
|---|---|---|---|
| | compound 32 | compound 34 | compound 36 |
| S.aureus FDA 209P | >100 | >100 | 100 |
| M.luteus ATCC 9341 | >100 | >100 | 100 |
| E.faecalis RIMD 3336001 | >100 | >100 | >100 |
| B.subtilis PCI 219 | >100 | >100 | 100 |
| E.coli NIHJ JC-2 | >100 | >100 | >100 |
| K.pneumoniae PCI 602 | >100 | >100 | >100 |
| P.aeruginosa IFO 3445 | >100 | >100 | >100 |

TABLE 8

| strain | MIC (µg/ml) | | |
|---|---|---|---|
| | compound 37 | compound 38 | compound 39 |
| S.aureus FDA 209P | >100 | >100 | >100 |
| M.luteus ATCC 9341 | >100 | >100 | >100 |
| E.faecalis RIMD 3336001 | >100 | >100 | >100 |
| B.subtilis PCI 219 | >100 | >100 | >100 |
| E.coli NIHJ JC-2 | >100 | >100 | >100 |
| K.pneumoniae PCI 602 | >100 | >100 | >100 |
| P.aeruginosa IFO 3445 | >100 | >100 | >100 |

TABLE 9

| strain | MIC (µg/ml) | | |
|---|---|---|---|
| | compound 40 | compound 41 | compound 47 |
| S.aureus FDA 209P | >100 | >100 | >100 |
| M.luteus ATCC 9341 | >100 | >100 | 50 |
| E.faecalis RIMD 3336001 | >100 | >100 | >100 |
| B.subtilis PCI 219 | >100 | >100 | >100 |
| E.coli NIHJ JC-2 | >100 | >100 | >100 |
| K.pneumoniae PCI 602 | >100 | >100 | >100 |
| P.aeruginosa IFO 3445 | >100 | >100 | >100 |

TABLE 10

| strain | MIC (µg/ml) | | |
|---|---|---|---|
| | compound 48 | compound 49 | compound 50 |
| S.aureus FDA 209P | 100 | >100 | >100 |
| M.luteus ATCC 9341 | >100 | >100 | >100 |
| E.faecalis RIMD 3336001 | >100 | >100 | >100 |
| B.subtilis PCI 219 | >100 | >100 | >100 |
| E.coli NIHJ JC-2 | >100 | >100 | >100 |
| K.pneumoniae PCI 602 | >100 | >100 | >100 |
| P.aeruginosa IFO 3445 | >100 | >100 | >100 |

TABLE 11

| strain | MIC (µg/ml) | | |
|---|---|---|---|
| | compound 51 | compound 53 | compound 54 |
| S.aureus FDA 209P | 100 | >100 | 100 |
| M.luteus ATCC 9341 | >100 | >100 | >100 |
| E.faecalis RIMD 3336001 | 100 | >100 | >100 |
| B.subtilis PCI 219 | >100 | >100 | >100 |
| E.coli NIHJ JC-2 | >100 | >100 | >100 |
| K.pneumoniae PCI 602 | >100 | >100 | >100 |
| P.aeruginosa IFO 3445 | >100 | >100 | >100 |

TABLE 12

| strain | MIC (µg/ml) | | |
|---|---|---|---|
| | compound 55 | amoxicillin | lansoprazol |
| S.aureus FDA 209P | >100 | 0.1 | >100 |
| M.luteus ATCC 9341 | >100 | ≦0.05 | >100 |
| E.faecalis RIMD 3336001 | >100 | 0.2 | >100 |
| B.subtilis PCI 219 | >100 | 0.2 | >100 |
| E.coli NIHJ JC-2 | >100 | 3.13 | >100 |
| K.pneumoniae PCI 602 | >100 | 50 | >100 |
| P.aeruginosa IFO 3445 | >100 | >100 | >100 |

As is clear from the above test results, the typical compounds of the present invention hardly exhibit antibacterial activity against the above-mentioned seven gram-positive or -negative strains. This means that the compounds of the present invention has selective antibacterial activity against Hp.

Thus, the compounds of the present invention have selective and effective antibacterial activities against the genus Helicobacter represented by Hp and have no antibacterial activities against intestinal bacteria such as E. coli, hardly cause any fluctuation of intestinal bacterial flora which may be caused in the case of other antibacterial agents such as penicillin and cephalosporin and are less dangerous of causing side effects such as enteritis and pseudomembranous colitis based on microbial substitution. Moreover, the compounds of the present invention exhibit the antibacterial activity selectively against the genus Helicobacter, so that they are deemed to hardly cause resistance induction for other strains, which is frequently seen in the case of existing antibacterial agents such as β-lactams and macrolides, as well as cross-resistance with other antibacterial agents.

Therefore, the compounds of the present invention can be applied as selective antibacterial agent against Hp for the treatment and prevention of reccurrence of peptic ulcer and chronic gastritis.

The compounds of the present invention may be administered to human orally or parenterally. In oral administration, the compounds may be in the form of tablets, coated tablets, powders, granules, capsules, microcapsules, syrups and the like; and in parenteral administration, in the form of injections which may include soluble freeze-drying form, suppositories and the like. In the preparation of these forms, pharmaceutically acceptable diluent bases, binders, lubricants, disintegrators, suspensions, emulsifiers, antiseptics, stabilizers and dispersing agents, for example, lactose, sucrose, starch, dextrin, crystalline cellulose, kaolin, calcium carbonate, talc, magnesium stearate, distilled water and physiological saline solution may be used.

BEST MODE FOR CARRYING OUT THE INVENTION

[Preparations and Examples]

The present invention is more specifically illustrated with reference to the following preparations and examples. It is to be, however, noted that the present invention is not limited to the preparations and examples.

Preparation 1: Preparation of 4-hydroxy-7-methoxyquinoline (1) m-Anisidine (12.3 g, 0.1 mol) is mixed with diethyl ethoxymethylenemalonate (21.6g, 0.1 mol) without solvent and stirred at 110°–120° C. for an hour with resulting ethanol being removed. The reactant was dissolved in diphenyl ether (150 ml) and further stirred at 230° C. for 4 hours with resulting ethanol being removed. The reaction mixture was allowed to cool to room temperature and was added with ethyl acetate (300 ml). The resulting precipitates were collected by filtration to obtain 12.4 g (50%) of ethyl 4-hydroxy-7-methoxy-3-quinolinecarboxylate.

NMR:δ 1.28(3H, t), 3.87(3H, s), 4.20(2H, q), 7.00(2H, m), 8.05(1H, d), 8.48(1H, s), 12.09(1H, brs)

(2) Ethyl 4-hydroxy-7-methoxy-3-quinolinecarboxylate (24.7 g, 0.1 mol) was hydrolysed with 2N aqueous solution of sodium hydroxide (250 ml) through boiling for 2 hours. The reaction mixture was allowed to cool to room temperature and adjusted with 2N hydrochloric acid to pH 5. The resulting precipitates were collected by filtration and washed with water. The precipitates were dried at 100°–120° C. for 3 hours in an oven and further dried under reduced pressure overnight over calcium chloride to obtain 21.4 g (98%) of 4-hydroxy-7-methoxy-3-quinolinecarboxylic acid.

NMR:δ 3.92(3H, s), 7.19(1H, d), 7.20(1H, dd), 8.19(1H, d), 8.82(1H, s), 13.15(1H, brs)

(3) 4-Hydroxy-7-methoxy-3-quinolinecarboxylic acid (21.4 g, 0.1 mol) was added with diphenyl ether (150 ml) and decarboxylated at 250° C. for 2 hours. The reaction mixture was allowed to cool to room temperature and added with ethyl acetate (300 ml). The resulting precipitates were collected by filtration to obtain crude 4-hydroxy-7-methoxyquinoline (15.0 g). This was recrystallized from water (about 300 ml) to obtain 14.8 g (86%) of 4-hydroxy-7-methoxyquinoline.

Melting Point: 215°–217° C.; MS m/z: 215 (M+); NMR:δ 3.87(3H, s), 6.20(1H, d), 6.87(1H, d), 6.91(1H, dd), 7.59 (1H, d), 8.23(1H, d), 11.30(1H, brs)

Starting from the corresponding substituted aniline, the following 4-hydroxyquinoline derivatives are obtained in accordance with the procedure of the Preparation 1.

4-Hydroxy-7-isopropylquinoline

MS m/z: 187 (M+);

4-Hydroxy-7-phenylquinoline

Melting Point: >300° C. (dec.); MS m/z: 221 (M+); NMR:δ 6.37(1H, d), 7.38–7.52(3H, m), 7.64–7.81(4H, m), 8.04(1H, d), 8.32(1H, d)

4-Hydroxy-7-iodoquinoline

Melting Point: >240° C. (dec.); MS m/z: 187 (M+); NMR:δ 6.04(1H, d), 7.61(1H, dd), 7.80–7.94(3H, m), 11.71 (1H, brs)

4-Hydroxy-7-phenoxymethylquinoline

Melting Point: 183°–184° C.; MS m/z: 251 (M+); NMR:δ 5.26(2H, s), 6.03(1H, d), 6.90–7.05(3H, m), 7.27–7.39(3H, m), 7.59(1H, s), 7.88(1H, d), 8.20(1H, d), 11.75(1H, brs)

7-N,N-Dimethylaminomethyl-4-hydroxyquinoline

MS m/z: 202 (M+); NMR(DMSO-d6)δ: 2.20(6H, s), 3.52 (2H, s), 6.00(1H, d), 7.24(1H, d), 7.45(1H, s), 7.86(1H, dd), 8.03(1H, d), 11.66(1H, brs)

7-(N-Isopropyl-N-methylamino)-4-hydroxyquinoline

Melting Point: 102°–104° C.; MS m/z: 216 (M+); NMR (DMSO-d6)δ: 1.16(6H, d), 2.73(3H, s), 4.20(1H, sept), 5.80(1H, d), 6.53(1H, d), 6.88(1H, dd), 7.64(1H, dd), 7.84 (1H, d), 11.16(1H, brs)

4-Hydroxy-7-morpholinoquinoline

Melting Point: >240° C.; MS m/z: 230 (M+); NMR (DMSO-d6)δ: 3.21–3.34(4H, m), 3.74–3.79(4H, m), 5.87 (1H, d), 6.73(1H, d), 7.04(1H, dd), 7.72(1H, t), 7.90(1H, d), 11.33(1H, brs)

4-Hydroxybenzo[h]quinoline

Melting Point: 256°–259° C. (dec.) MS m/z: 195 (M+); NMR(DMSO-d6)δ: 6.27(1H, d), 7.71–7.77(3H, m), 7.96 (1H, dd), 8.04(1H, m), 8.12(1H, d), 8.63–8.67(1H, m), 12.15(1H, brs)

4-Hydroxy-7,8,9,10-tetrahydrobenzo[h]quinoline

Melting Point: 263°–265° C. (dec.); MS m/z: 199 (M+); NMIR(DMSO-d6)δ: 1.73–1.99(4H, m), 2.76–2.85(4H, m), 6.03(1H, d), 7.01(1H, d), 7.74(1H, dd), 7.86(1H, d), 10.89 (1H, brs)

7-Benzylthio-4-hydroxyquinoline

Melting Point: 173°–176° C.; MS m/z: 267 (M+); NMR (DMSO-d6)δ: 4.35(2H, s), 5.98(1H, d), 7.22–7.45(7H, m), 7.83(1H, dd), 7.94(1H, d), 11.61(1H, brs)

4-Hydroxy-7-phenoxyquinoline

Melting Point: 176°–179° C.; MS m/z: 237 (M+); NMR (DMSO-d6)δ: 5.96(1H, d), 6.90(1H, d), 6.99(1H, dd), 7.17 (2H, d), 7.26(1H, t), 7.48(2H, t), 7.80(1H, d), 8.08(1H, d), 11.54(1H, brs)

4-Hydroxy-8-methylquinoline

Melting Point: 209°–210° C. (dec.); MS m/z: 159 (M+); NMR(DMSO-d6)δ: 2.48(3H, s), 6.06(1H, d), 7.20(1H, t), 7.47(1H, dd), 7.81(1H, t), 7.97(1H, dd), 11.06(1H, brs)

4-Hydroxy-7,8-dimethylquinoline

Melting Point: >300° C.; MS m/z: 173 (M+); NMR (DMSO-d6)δ: 2.37(3H, s), 2.38(3H, s), 6.01(1H, d), 7.14 (1H, d), 7.79(1H, t), 8.86(1H, d), 10.99(1H, brs)

4-Hydroxy-8-methoxyquinoline

Melting Point: 165°–169° C.; MS m/z: 175 (M+); NMR (DMSO-d6)δ: 3.97(3H, s), 6.03(1H, d), 7.17–7.24(2H, m), 7.63(1H, dd), 7.72(1H, dd), 11.30(1H, brs)

4-Hydroxy-1,7-phenanthroline

Melting Point: 293°–295° C. (dec.); MS m/z: 196 (M+); NMR(DMSO-d6)δ: 6.42(1H, brs), 7.74(1H, dd), 7.83(1H,d), 8.10(1H, brs), 8.35(1H, d), 9.05(1H, dd), 9.14(1H, dd), 12.26(1H, brs)

4-Hydroxy-,10-phenanthroline

Melting Point: 198°–202° C.; MS m/z: 196 (M+); NMR (DMSO-d6)δ: 6.38(1H, dd), 7.86(1H, d), 7.89(1H, dd), 8.03(1H, dd), 8.25(1H, d), 8.61(1H, dd), 9.14(1H, dd), 12.47(1H, brs)

Preparation 2: Preparation of trans-4-hydroxy-7-styrylquinoline

4-Hydroxy-7-iodoquinoline (1.08 g, 4.0 mmol) obtained in the Preparation 1, styrene (0.50 g, 4.8 mmol), tri-n-butylamine (0.89 g, 4.8 mmol), palladium acetate (18 mg, 0.08 mmol) and triphenylphosphine (42 mg, 0.16 mmol) were reacted in dimethylformamide (DMF; 30 ml) at 120° C. for 2 hours. The resulting reactant was added with water (100 ml) and the precipitates were collected by filtration and dried over calcium chloride. The obtained powder was purified through silica gel column chromatography (Wako Gel™ C-200, methylene chloride : methanol=9 : 1) to obtain the titled compound (490 mg, 50%).

Melting Point: >250° C. (dec.); MS m/z: 247 (M+); NMR(DMSO-d6)δ: 6.02(1H, d), 7.2–7.5(5H, m), 7.6–7.7 (4H, m), 7.87(1H, d), 8.07(1H, d), 11.74(1H, brs)

Preparation 3: Preparation of 4-hydroxy-7-phenethylquinoline trans-4-Hydroxy-7-styrylquinoline (280 mg, 1.13 mmol) obtained in the Preparation 2 was dissolved in ethanol (200 ml), hydrogenated in the presence of 10% palladium on activated carbon (100 mg) and purified through silica gel column chromatography (Wako Gel™ C-200, methylene chloride : methanol=9 : 1) to obtain the titled compound (220mg, 78%).

Melting Point: 204°–205° C.; FAB-MS m/z: 250 [M+H]$^+$; NMR(DMSO-d$_6$)δ: 2.93–2.99(4H, m), 6.98(1H, d), 7.17–7.30(7H, m), 7.82(1H, dd), 7.98(1H, d), 11.58(1H, brs)

Preparation 4: Preparation of 4-hydroxy-7-dodecylquinoline

Dodecene was used instead of styrene in the Preparation 2 and the procedure was made in accordance with the Preparation 2 and 3 to obtain the titled compound.

Melting Point: 90°–91.5° C.; MS m/z: 313 (M$^+$); NMR (DMSO-d$_6$)δ: 0.85(1H, t), 1.23–1.29(18H, m), 1.58–1.64 (2H, m), 2.68(2H, t), 5.97(1H, d), 7.14(1H, d), 7.28(1H, s), 7.83(1H, d), 7.98(1H, d), 11.59(1H, brs)

Preparation 5: Preparation of 4-hydroxy-7-(4-methoxycarbonyl-1-piperazinyl)quinoline A mixture of 3-(4-methoxycarbonyl-1-piperazinyl)aniline (0.75 g, 3.2 mmol), ethyl orthoformate (0.50 g, 3.4 mmol), Meldrum's acid (0.48 g, 3.4 mmol) was stirred at 110° C. for 1.5 hours. The reaction mixture was added with diphenyl ether (10 ml) and stirred at 240° C. for 1.5 hours. After allowing to cool, n-hexane was added to the mixture. The resulting precipitates were collected by filtration and purified by column chromatography (Wako Gel™ C-200, methylene chloride methanol=10 : 1) to obtain the titled compound (320 mg, 35%).

Melting Point:>240° C.; MS m/z: 287 (M$^+$); NMR (DMSO-d$_6$)δ: 3.28(4H, t), 3.54(4H, t), 3.64(3H, s), 5.86(1H, d), 6.74(1H, d), 7.03(1H, dd), 7.71(1H, dd), 7.90(1H, d), 11.32(1H, brs)

Preparation 6: Preparation of 4-chloro-7-methoxyquinoline

4-Hydroxy-7-methoxy-3-quinolinecarboxylic acid (7.56 g, 4 mmol) obtained in (2) of the Preparation 2 was added with diphenyl ether (100 ml) and decarboxylated through heating at 250° C. for 2 hours. After allowing to cool to room temperature, the reactant was added with phosphorus oxychloride (2 ml) and heated at 130° C. for an hour. After allowing to cool, the reactant was poured into ice water (200 ml) and extracted twice with ethyl acetate (200 ml). The extracted solutions with ethyl acetate were combined and washed three times with 2N hydrochloric acid (100 ml). The solution washed with the hydrochloric acid was combined with the above-mentioned water layer and adjusted by 2N aqueous solution of sodium hydroxide to pH 9. The resulting precipitates were collected by filtration to obtain 5.37 g (80%) of 4-chloro-7-methoxyquinoline.

Melting Point: 86°–88° C.; MS m/z: 193 (M$^+$); NMR:δ 3.97(3H, s), 7.29(1H, dd), 7.35(1H, d), 7.43(1H, d), 8.12 (1H, d), 8.69(1H, d)

Starting from the various substituted aniline, the procedure was made in accordance with (1) and (2) of the Preparation 1 to obtain 4-hydroxyquinoline-3-carboxylic acid derivatives. Using these derivatives, the procedure was made in accordance with the Preparation 6 to obtain the following 4-haloquinoline derivatives.

4-Chloro-5-methylquinoline

Melting Point: 77-81° C.; MS m/z: 177 (M$^+$); NMR:δ 3.05(3H, s), 7.38(1H, dd), 7.45(1H, d), 7.59(1H, dd), 7.98 (1H, dd), 8.68(1H, d)

4-Chloro-7-methylquinoline

Melting Point: 28° C.; MS m/z: 177 (M$^+$); NMR:δ 2.59 (3H, s), 7.43(1H, d), 7.48(1H, dd), 7.90(1H, d), 8.12(1H, d), 8.74(1H, d)

4-Chloro-7-nitroquinoline

Melting Point: 171°–173° C.; MS m/z: 208 (M$^+$); NMR:δ 7.68(1H, d), 8.42(2H, d), 8.96(1H, d), 9.03(1H, t)

7-Carbamoyl-4-chloroquinoline

Melting Point: 241°–242° C. (dec.); MS m/z: 206 (M$^+$);

7-Acetyl-4-chloroquinoline

Melting Point: 114°–118° C.; MS m/z: 205 (M$^+$); NMR:δ 2.78(3H, s), 7.60(1H, d), 8.21(1H, dd), 8.31(1H, d), 8.69 (1H, d), 8.88(1H, d)

4-Chloro-7-hydroxymethylquinoline

Melting Point: 138°–139° C.; MS m/z: 193 (M$^+$); NMR:δ 4.77(2H, d), 5.50(1H, t), 7.70(2H, m), 8.03(1H, s), 8.16(1H, d), 8.82(1H, d)

4-Chloro-7-n-hexylquinoline

MS m/z: 247 (M$^+$); NMR:δ 0.88(3H, t), 1.30(6H, m), 1.70(2H, m), 2.84(2H, t), 7.42(1H, d), 7.50(1H, dd), 7.90 (1H, d), 8.14(1H, d), 8.74(1H, d)

4-Chloro-7-methoxymethylquinoline

MS m/z: 207 (M$^+$); NMR:δ 3.46(3H, s), 4.69(2H, s), 7.48(1H, d), 7.66(1H, d), 8.06(1H, s), 8.23(1H, d), 8.78(1H, d)

4-Chloro-7-methylthioquinoline

Melting Point: 72.5°–73.5° C.; MS m/z: 209 (M$^+$); NMR:δ 2.62(3H, s), 7.40(1H, d), 7.49(1H, dd), 7.79(1H, d), 8.09(1H, d), 8.71(1H, d)

4-Chloro-7-N,N-dimethylaminoquinoline

Melting Point: 153.0°–154.5° C.; MS m/z: 206 (M$^+$); NMR(CDCl$_3$):δ 3.12(6H, s), 7.15–7.26(3H, m), 8.04(1H,d), 8.59(1H, d)

4-Chloro-7-isopropylthioquinoline

MS m/z: 237 (M$^+$); NMR(CDCl$_3$):δ 1.42(6H, d), 3.68 (1H, sept), 7.42(1H, dd), 7.53(1H, d), 7.98(1H, d), 8.11 (1H, d), 8.74(1H, d)

7-Benzyl-4-chloroquinoline

MS m/z: 253 (M$^+$); NMR(CDCl$_3$):δ 4.20(2H, s), 7.20–7.40(5H, m), 7.43(1H, d), 7.48(1H, dd), 7.93(1H, d), 8.13(1H, d), 8.73(1H, d)

7-(2-Naphthyl)-4-chloroquinoline

Melting Point: 119°–121° C.; MS m/z: 289 (M$^+$); NMR (CDCl$_3$):δ 7.48(1H, d), 7.52(2H, m), 7.80–8.00(4H, m), 8.04(1H, dd), 8.20(1H, s), 8.31(1H, d), 8.46(1H, d), 8.81 (1H, d)

Preparation 7: Preparation of 4,7-dichloro-2,3-dihydrofuro [2,3-b]quinoline

The titled compound was obtained from 2,4,7-trichloro-3-(β-chloroethyl) quinoline in accordance with an Example shown in Japanese Patent Publication (Kokoku) No. 47-43952.

Melting Point: 98° C.; MS m/z: 239 (M$^+$); NMR:δ 3.41 (2H, t), 4.76(2H, t), 7.36(1H, dd), 7.80(1H, d), 7.91(1H, d)

Preparation 8: Preparation of 4-chloro(bromo)-7-ethoxyquinoline (1) 7-Methoxy-4-chloroquinoline(13 g, 67 mmol) was refluxed for 24 hours with 47% hydrobromic acid (30 ml). After allowing to cool, aqueous solution of saturated sodium bicarbonate was added for neutralization and the resulting crystals were filtered. The obtained crystals were washed with water, sufficiently dried and recrystallized from ethanol to obtain 9 g of 4-chloro(bromo)-7-hydroxyquinoline [a mixture of 4-chloro-7-hydroxyquinoline and 4-bromo-7-hydroxy-quinoline (7 : 3)]. This mixture was used without further purification as the starting material in a next reaction.

MS m/z: 179 (M$^+$, 4-Cl derivative) and 223 (M$^+$, 4-Br derivative)

(2) 4-Chloro(bromo)-7-hydroxyquinoline (200 mg) dissolved in N,N-dimethylformamide (DMF; 30 ml) was added with potassium carbonate (203 mg) and ethyl iodide (232 mg) and stirred at room temperature for 8 hours. The reaction mixture was added with water (50 ml) and methylene chloride (30 ml) and shaken to separate the organic layer. Further, the water layer was extracted three times with methylene chloride (30 ml). This extract solution was combined with the above-mentioned organic layer, washed with saturated saline solution and dried over magnesium sulfate. This extract solution was detected by thin-layer chromatography (TLC; MERCK, Art. 5554, methylene chloride : methanol=9 : 1) to find UV (254 nm) absorptive spots at Rf values of 0.7 and 0.4. After drying, the solvent was removed under reduced pressure from the extract solution. The residue was chromatographed by silica gel column chromatography (Wako Gel™ C-200, methylene chloride : methanol=9 : 1). Fractions corresponding to Rf value of 0.7 were collected and evaporated to obtain the aimed 4-chloro (bromo)-7-ethoxy-quinoline (185 mg). MS m/z: 207 ($M^+$, 4-Cl derivative) and 251($M^+$, 4-Br derivative)

Corresponding various halides were reacted, in accordance with the procedure of (2) in the Preparation 8, with 4-chloro (bromo)-7-hydroxyquinoline to obtain corresponding 4-chloro (bromo)-7-substituted quinolines.

4-Chloro(bromo)-7-isopropoxyquinoline
  MS m/z: 221 ($M^+$, 4-Cl derivative) and 265($M^+$, 4-Br derivative)
4-Chloro(bromo)-7-n-hexyloxyquinoline
  MS m/z: 263 ($M^+$, 4-Cl derivative) and 307($M^+$, 4-Br derivative)
7-Benzyloxy-4-chloro(bromo)quinoline
  MS m/z: 269 ($M^+$, 4-Cl derivative) and 313($M^+$, 4-Br derivative)
4-Chloro(bromo)-7-n-propoxyquinoline
  MS m/z: 221 ($M^+$, 4-Cl derivative) and 265($M^+$, 4-Br derivative)
4-Chloro(bromo)-7-methanesulfonyloxyquinoline
  MS m/z: 257 ($M^+$, 4-Cl derivative) and 301($M^+$, 4-Br derivative)
4-Chloro(bromo)-7-dodecyloxyquinoline
  MS m/z: 347 ($M^+$, 4-Cl derivative) and 391($M^+$, 4-Br derivative)
4-Chloro(bromo)-7-octyloxyquinoline
  MS m/z: 291 ($M^+$, 4-Cl derivative) and 335($M^+$, 4-Br derivative)
4-Chloro(bromo)-7-(5-ethoxycarbonyl-n-pentyloxy) quinoline
  MS m/z: 321 ($M^+$, 4-Cl derivative) and 366($M^+$, 4-Br derivative)

Preparation 9: Preparation of 4-hydroxy-8-nitroquinoline

4-Hydroxyquinoline (1.45 g, 10 mmol) was dissolved in 3 ml of concentrated sulfuric acid and the solution was cooled −10° C. or less. The solution was gradually added with mixed acid (0.8 ml of concentrated nitric acid with 1.2 ml of concentrated sulfuric acid) such that the reaction solution was not elevated in temperature up to 0° C. or more, and stirred at 0° C. for 3 hours. The reaction mixture was poured into crashed ice and neutralized with 2N aqueous solution of sodium hydroxide. The resulting precipitates were filtered off and washed with water. The filtrate was combined with the washing solution and extracted with methylene chloride. After drying over anhydrous magnesium sulfate, the solvent was removed under reduced pressure. The residue was developed by silica gel column chromatography (Wako Gel™ C-200, methylene chloride : methanol=20 : 1). Firstly eluted yellow fractions were collected and the solvent was removed to obtain 380 mg (20%) of 4-hydroxy-8-nitroquinoline.

Melting Point: 204°–205.5° C.; MS m/z: 190 ($M^+$); NMR:δ 6.24(1H, d), 7.51(1H, dd), 7.97(1H, d), 8.56(1H, dd), 8.64(1H, dd), 11.86(1H, brs)

Preparation 10: Preparation of 7-(2-benzimidazolyl)-thiomethyl-4-chloroquinoline (1) Commercially available 4-chloro-7-(trifluoromethyl)-quinoline (8 g, 0.035 mol) was added under ice cooling with 30% fuming sulfuric acid (35 ml) and stirred at 100° C. for 5 hours. After allowing to cool to room temperature, the reactant was poured into ice water and made basic enough with excess concentrated ammonia water, and insoluble materials were filtered off. The filtrate was adjusted by 2N hydrochloric acid to pH 3–4. The resulting jellied precipitate was collected by filtration, washed with ethanol (50 ml) and dried under reduced pressure over phosphorus pentoxide to obtain 5.4 g (74%) of 7-carboxy-4-chloroquinoline.

Melting Point: >235° C.; MS m/z: 207 ($M^+$);

(2) 7-Carboxy-4-chloroquinoline (5 g, 24.0 mmol) was dissolved in a mixed solution of potassium hydroxide (1.49 g, 26.6 mmol) with methanol (150 ml) and stirred at room temperature overnight. The reactant was evaporated to dryness under reduced pressure. The residue was added with dimethylformamide (DMF; 60 ml) and methyl iodide (3.5 g, 24.6 mmol) in the order named and stirred at 80° C. for an hour. The reaction mixture was poured into ice water. The resulting precipitates were collected by filtration, dried over phosphorus pentoxide and recrystallized from ethanol (20 ml) to obtain 3.6 g (61%) of 7-methoxycarbonyl-4-chloroquinoline.

Melting Point: 118°–119° C.; MS m/z: 221 ($M^+$); NMR:δ 4.00(3H, s), 7.82(1H, d), 8.26(1H, dd), 8.38(1H, d), 8.73 (1H, d), 8.95(1H, d)

(3) 7-Methoxycarbonyl-4-chloroquinoline(3.75 g, 0.017 mol) was dissolved in methanol (200 ml), added under ice-cooling with sodium borohydride (12.9 g, 0.34 mol) and stirred for an hour. The reaction mixture was poured into ice water. The resulting precipitates were collected by filtration, dried over phosphorus pentoxide and recrystallized from chloroform (20 ml) to obtain 1.0 g (30%) of 7-hydroxymethyl-4-chloroquinoline.

Melting Point: 138°–139° C.; MS m/z: 193 ($M^+$); NMR:δ 4.77(2H, d), 5.50(1H, t), 7.70(2H, m), 8.03(1H, s), 8.16(1H, d), 8.82(1H, d)

(4) 7-Hydroxymethyl-4-chloroquinoline (930 mg, 4.82 mmol) dissolved in anhydrous methylene chloride (40 ml) was added with triethylamine (679 mg, 6.72 mmol). The mixture was cooled in dry ice/acetone bath, added dropwise with methanesulfonyl chloride (770 mg, 6.7 mmol) and the reactant was stirred for 20 minutes without the cooling bath. Then, the reactant was added under ice-water cooling with cool aqueous solution of saturated sodium bicarbonate (40 ml) and ethyl acetate (150 ml) and shaken to separate the organic layer. The separated organic layer was washed with saturated saline solution and dried over magnesium sulfate. The solvent was removed to obtain 7-methanesulfonylmethyl-4-chloroquinoline as oily product.

MS m/z: 271 ($M^+$); NMR: δ3.03(3H, s), 5.46(2H, s), 7.54(1H, d, J=4.6 Hz), 7.71(1H, d, J=8.9 Hz), 8.15(1H, s), 8.30(1H, d, J=8.9 Hz), 8.82(1H, d, J=4.6 Hz)

The obtained 7-methanesulfonylmethyl-4-chloroquinoline was dissolved in ethanol (70 ml), added under ice-water cooling with 2-mercaptobenzimidazole (724 mg, 4.82 mmol), and stirred for 30 minutes at the same temperature, and further stirred for 30 minutes without the cooling bath. The reactant was added with excess water and 2N hydrochloric acid (40 ml) and washed with ethyl acetate. The water layer was adjusted by 2N aqueous solution of sodium hydroxide to pH 9–10 and extracted three times with methylene chloride (200 ml). The extract solution was dried over magnesium sulfate and the solvent was removed under reduced pressure. The residue was purified by silica gel column chromatography (Wako Gel™ C-200, methylene chloride : methanol=20 : 1) to obtain 700 mg (45%) of the titled compound.

Melting Point: 165°–167° C. (dec.); MS m/z: 325 (M$^+$); NMR:δ 4.82(2H, s), 7.12(2H, m), 7.45(2H, br), 7.71(1H, d), 7.86(1H, d), 8.15(1H, s), 8.15(1H, d), 8.80(1H, d), 12.60 (1H, brs)

Example 1:

7-Methoxyquinoline-4(1H)-thione (compound 1)

4-Hydroxy-7-methoxyquinoline (2.3 g, 13 mmol) dissolved in pyridine (30 ml) was added with phosphorus pentasulfide (2.9 g, 13 mmol) and refluxed for an hour. The reaction mixture was allowed to cool to room temperature and the solvent was removed under reduced pressure. The residues were added with water (80 ml) and stood at 0° C. for about 30 minutes. The resulting precipitates were collected by filtration, washed with water and recrystallized from mixed solvent (about 60 ml) of ethanol with water (2 : 1) to obtain 1.7 g (68%) of the titled orange compound.

Melting Point: 196°–201° C.; MS m/z: 191 (M$^+$); NMR (DMSO-d$_6$)δ: 3.89(3H, s), 7.01(1H, d, J=2.3 Hz), 7.10(1H, dd, J=2.3, 9.2 Hz), 7.16(1H, d, J=6.9 Hz), 7.75(1H, dd, J=6.3, 6.9 Hz), 8.60(1H, d, J=9.2 Hz), 12.60(1H, brs)

In accordance with the procedure of the Example 1, the following compounds were obtained from corresponding starting materials.

7-Isopropylquinoline-4(1H)-thione (Compound 2)

Melting Point: 167°–176° C. (dec.) MS m/z: 203 (M$^+$); NMR(DMSO-d$_6$)δ: 1.27(6H, d, J=6.9 Hz), 3.10(1H, m), 7.24(1H, d, J=6.6 Hz), 7.39(1H, d, J=8.6 Hz), 7.45(1H, s), 7.80(1H, d, J=6.6 Hz), 8.60(1H, d, J=8.6 Hz), 12.76(1H, brs)

7-Phenylquinoline-4(1H)-thione (Compound 3)

Melting Point: 166-174° C.; MS m/z: 237 (M$^+$); NMR (DMSO-d$_6$)δ: 7.39–7.52(5H, m), 7.62–7.67(4H, m), 8.90 (1H, d, J=8.9 Hz)

7-Phenoxymethylquinoline-4(1H)-thione (Compound 6)

Melting Point: 186°–189° C.; MS m/z: 267 (M$^+$); NMR (DMSO-d$_6$)δ: 5.30(2H, s), 6.94–7.35(6H, m), 7.52(1H, d, J=8.6 Hz), 7.71(1H, s), 7.84(1H, t, J=5.6, 6.6 Hz), 8.73(1H, d, J=8.6 Hz), 12.9(1H, brs)

8-Nitroquinoline-4(1H)-thione (Compound 7)

Melting Point: 189°–192° C.; MS m/z: 206 (M$^+$); NMR (DMSO-d$_6$)δ: 7.42(1H, d, J=6.9 Hz), 7.62(1H, dd, J=8.3, 8.3 Hz), 7.85(1H, d, J=6.9 Hz), 8.72(1H, dd, J=1.3, 8.3 Hz), 9.11(1H, dd, J=1.3, 8.3 Hz), 12.64(1H, brs)

7-Dodecylquinoline-4(1H)-thione (Compound 30)

Melting Point: 107°–109° C.; MS m/z: 329 (M$^+$); NMR (DMSO-d$_6$)δ: 0.85(3H, t, J=6.6 Hz), 1.23–1.30(18H, m), 1.55–1.68(2H, m), 2.72(2H, t, J=7.6 Hz), 7.23(1H, d, J=6.3 Hz), 7.32(1H, d, J=8.6 Hz), 7.41(1H, s), 7.80(1H, t, J=6.3 Hz), 8.58(1H, d, J=8.6 Hz), 12.75(1H, brs)

7-Phenethylquinoline-4(1H)-thione (Compound 31)

Melting Point: 188°–192° C.; FAB-MS m/z: 266 [M+H]$^+$; NMR(DMSO-d$_6$)δ: 2.9–3.1(4H, m), 7.1–7.5(8H, m), 7.78 (1H, d, J=6.9 Hz), 8.57(1H, d, J=8.2 Hz), 12.76(1H, brs)

trans-7-Styrylquinoline-4(1H)-thione (Compound 32)

Melting Point: 238°–240° C.; FAB-MS m/z: 264 [M+H]$^+$; NMR(DMSO-d$_6$)δ: 7.26(1H, d, J=6.6 ), 7.3–7.8(9H, m), 7.83(1H, d, J=6.6 Hz), 8.65(1H, d, J=8.6 Hz), 12.87(1H, brs)

7-N,N-Dimethylaminomethylquinoline-4(1H)-thione (Compound 33)

Melting Point: 135°–140° C. (dec.); MS m/z: 218 (M$^+$); NMR(DMSO-d$_6$)δ: 2.78(6H, s), 4.48(2H, s), 7.32(1H, d, J=5.7 Hz), 7.53(1H, d, J=8.4 Hz), 7.83(1H, brd, J=5.7 Hz), 8.30(1H, s), 8.70(1H, d, J=8.4 Hz), 13.55(1H, brs)

7-(N-Isopropyl-N-methylamino)quinoline-4(1H)-thione (Compound 34)

Melting Point: 185°–188° C.; MS m/z: 232 (M$^+$); NMR (DMSO-d$_6$)δ: 1.18(6H, d, J=6.4 Hz), 2.81(3H, s), 4.25(1H, sept, J=6.4 Hz), 6.58(1H, d, J=2.5 Hz), 6.95(1H, d, J=6.5 Hz), 7.12(1H, dd, J=2.5, 9.6 Hz), 7.58(1H, t, J=6.5 Hz), 8.44(1H, d, J=9.6 Hz), 12.23(1H, brs)

7-Morpholinoquinoline-4(1H)-thione (Compound 36)

Melting Point: 243°–247° C. (dec.); MS m/z: 246 (M$^+$); NMR(DMSO-d$_6$)δ: 3.29(4H, t, J=4.8 Hz), 3.77(4H, t, J=4.8 Hz), 6.78(1H, d, J=2.4 Hz), 7.04(1H, dd, J=1.0, 6.5 Hz), 7.26(1H, dd, J=2.4, 9.5 Hz), 7.66(1H, t, J=6.5 Hz), 8.49(1H, d, J=9.5 Hz), 12.41(1H, brs)

7-Benzylthioquinoline-4(1H)-thione (Compound 37)

Melting Point: 171°–175° C.; MS m/z: 283 (M$^+$); NMR (DMSO-d$_6$)δ: 4.32(2H, s), 6.29(1H, d, J=4.6 Hz), 7.21–7.57 (7H, m), 7.72(1H, dd, J=1.6, 3.8 Hz), 8.21(1H, d, J=8.5 Hz), 13.02(1H, brs)

7-Phenoxyquinoline-4(1H)-thione (Compound 38)

Melting Point: 168°–171° C.; FAB-MS m/z: 254 [M+H]$^+$; NMR(DMSO-d$_6$)δ: 6.98(1H, d, J=2.3 Hz), 7.17–7.23(4H, m), 7.30(1H, t, J=7.4 Hz), 7.48–7.55(2H, m), 7.76(1H, brd, J=5.6 Hz), 8.68(1H, d, J=9.2 Hz), 12.64(1H, brs)

Benzo[h]quinoline-4(1H)-thione (Compound 39)

Melting Point: 223°–227° C. (dec.); MS m/z: 211 (M$^+$); NMR(DMSO-d$_6$)δ: 7.51(1H, d, J=6.6 Hz), 7.75–7.89(4H, m), 8.03–8.10(1H, m), 8.72–8.77(2H, m), 13.18(1H, brs)

7,8,9,10-Tetrahydrobenzo[h]quinoline-4(1H)-thione (Compound 40)

Melting Point: 212°–214° C. (dec.); MS m/z: 215 (M$^+$); NMR(DMSO-d$_6$)δ: 1.76–1.92(4H, m), 2.8–2.9(4H, m), 7.17 (1H, d, J=8.6 Hz), 7.28(1H, d, J=6.6 Hz), 7.68(1H, t, J=6.6 Hz), 8.48(1H, d, J=8.6 Hz), 11.95(1H, brs)

8-Methylquinoline-4(1H)-thione (Compound 41)

Melting Point: 223°–227° C.; MS m/z: 175 (M$^+$); NMR (DMSO-d$_6$)δ: 2.55(3H, s), 7.33(1H, d, J=6.6 Hz), 7.35(1H, dd, J=7.3, 8.6 Hz), 7.58(1H, dd, J=1.0, 7.3 Hz), 7.74(1H, d, J=6.6 Hz), 8.58(1H, dd, J=1.0, 8.6 Hz), 12.14(1H, brs)

8-Methoxyquinoline-4(1H)-thione (Compound 42)

Melting Point: 195°–199° C.; MS m/z: 191 (M$^+$); NMR (DMSO-d$_6$)δ: 4.03(3H, s), 7.27–7.41(3H, m), 7.66(1H, brs), 8.25(1H, dd, J=1.0, 8.3 Hz), 12.47(1H, brs)

1,7-Phenanthroline-4(1H)-thione (Compound 44)

Melting Point: 210°–220° C. (dec.); MS m/z: 212 (M$^+$); NMR(DMSO-d$_6$)δ: 7.53(1H, d, J=6.6 Hz), 7.79(1H, dd, J=4.3, 8.6 Hz), 7.92(1H, d, J=6.6 Hz), 7.93(1H, d, J=9.6 Hz), 9.00(1H, d, J=9.6 Hz), 9.09(1H, dd, J=1.3, 4.3 Hz), 9.17(1H, dd, J=1.3, 8.6 Hz), 13.33(1H, brs)

1,10-Phenanthroline-4(1H)-thione (Compound 45)

Melting Point: 245°–250° C. (dec.); MS m/z: 212 (M$^+$); NMR(DMSO-d$_6$)δ: 7.63(1H, dd, J=1.0, 6.6 Hz), 7.94(1H, t, J=6.6 Hz), 7.95(1H, dd, J=4.3, 8.3 Hz), 8.00(1H, d, J=8.9 Hz), 8.65(1H, dd, J=1.7, 8.3 Hz), 8.86(1H, d, J=8.9 Hz), 9.18(1H, dd, J=1.7, 4.3 Hz), 13.55(1H, brs)

7,8-Dimethylquinoline-4(1H)-thione (Compound 55)

Melting Point: 204°–209° C.; MS m/z: 189 (M$^+$); NMR (DMSO-d$_6$)δ: 2.41(3H, s), 2.43(3H, s), 7.27(1H, d, J=6.6 Hz), 7.30(1H, d, J=8.9 Hz), 7.72(1H, d, J=6.6 Hz), 8.49(1H, d, J=8.9 Hz)

Example 2:

7-Methoxyquinoline-4(1H)-thione (Compound 1)

4-Chloro-7-methoxyquinoline(965 mg, 5 mmol) and 70% sodium hydrosulfide (800 mg, 10 mmol) were added to ethanol (100 ml) and stirred at room temperature for 6 days. Ethanol was removed under reduced pressure from the reaction mixture. The residue was chromatographed by silica gel column chromatography, eluted with mixed solution of methylene chloride with methanol (16 : 1) for collection of yellow bands. The solvent was removed and the residue was added with a small amount of methylene chloride. The resulting precipitates were collected by filtration to obtain 590 mg (62%) of the titled compound. This compound was completely the same as the compound 1 obtained in the Example 1.

In accordance with the procedure of the Example 2, the following compounds were obtained from corresponding starting materials.

5-Methylquinoline-4(1H)-thione (Compound 10)

Melting Point: >80° C.; MS m/z: 175 (M$^+$); NMR (DMSO-d$_6$)δ: 3.11(3H, s), 7.15(1H, m), 7.27(1H, d, J=6.9 Hz), 7.46–7.54(2H, m), 7.59(1H, d, J=6.9 Hz), 12.61(1H, brs)

7-Methylquinoline-4(1H)-thione (Compound 11)

Melting Point: 151°–153° C.; MS m/z: 175 (M$^+$); NMR (CD30D)δ: 2.61(3H, s), 7.45(1H, dd, J=1.3, 8.6 Hz), 7.50 (1H, d, J=1.3 Hz), 7.55(1H, d, J=6.6 Hz), 7.82(1H, d, J=6.6 Hz), 8.80(1H, d, J=8.6 Hz)

7-Carbamoylquinoline-4(1H)-thione (Compound 12)

Melting Point: 171°–173° C.; MS m/z: 204 (M$^+$); NMR (DMSO-d$_6$)δ: 7.34(1H, d, J=7 OHz), 7.65(1H, brs), 7.85–7.90(2H, m), 8.13(1H, s), 8.23(1H, brs), 8.68(1H, d, J=8.6 ), 13.00(1H, brs)

7-Acetylquinoline-4(1H)-thione (Compound 13)

Melting Point: 205°–215° C. (dec.); MS m/z: 203 (M$^+$); NMR(CD$_3$OD)δ: 3.09(3H, s), 7.92(1H, d, J=6.9 Hz), 8.20 (1H, d, J=6.9 Hz), 8.38(1H, dd, J=1.7, 8.6 Hz), 8.59(1H, d, J=1.7 Hz), 9.27(1H, d, J=8.6 Hz)

7-Hydroxymethylquinoline-4(1H)-thione (Compound 14)

Melting Point: 180°–185° C.; MS m/z: 191 (M$^+$); NMR (DMSO-d$_6$)δ: 4.66(2H, s), 7.26(1H, d, J=6.6 Hz), 7.35(1H, d, J=8.6 Hz), 7.61(1H, s), 7.80(1H, dd, J=4.0, 6.6 Hz), 8.60(1H, d, J=8.6 Hz), 12.85(1H, brs)

7-n-Hexylquinoline-4(1H)-thione (Compound 15)

Melting Point: 118°–121° C.; MS m/z: 245 (M$^+$); NMR (DMSO-d$_6$)δ: 0.92(3H, t, J=6.9 Hz), 1.35(6H, m), 1.69(2H, m), 2.78(2H, t, J=7.3 Hz), 7.30(1H, d, J=6.3 Hz), 7.39(1H, dd, J=1.3, 8.6 Hz), 7.48(1H, d, J=1.3 Hz), 7.86(1H, d, J=6.3 Hz), 8.63(1H, d, J=8.6 Hz), 12.82(1H, brs)

7-Methoxymethylquinoline-4(1H)-thione (Compound 16)

MS m/z: 205 (M$^+$); NMR(CDCl$_3$)δ: 3.43(3H, s), 4.55(2H, s), 7.39(1H, dd, J=1.3, 8.6 Hz), 7.45(1H, d, J=6.8 Hz), 7.50(1H, d, J=6.8 Hz), 7.62(1H, s), 8.81(1H, d, J=8.6 Hz)

7-Methylthioquinoline-4(1H)-thione (Compound 17)

Melting Point: 191°–194° C.; MS m/z: 207 (M$^+$); NMR (DMSO-d$_6$)δ: 2.58(3H, s), 7.20(1H, d, J=6.6 Hz), 7.33(1H, dd, J=2.0, 8.9 Hz), 7.36(1H, d, J=2.0 Hz), 7.78(1H, m), 8.55(1H, d, J=8.9 Hz), 12.71(1H, brs)

7-Chloro-2,3-dihydrofuro[2,3-b]quinoline-4(1H)-thione (Compound 18)

Melting Point: 284°–286° C.; MS m/z: 237 (M$^+$); NMR (DMSO-d$_6$)δ: 3.23(2H, t, J=8.5 Hz), 3.53(2H, t, J=8.5 Hz), 7.21(1H, dd, J=2.0, 8.5 Hz), 7.35(1H, d, J=2.0 Hz), 7.36(1H, d, J=8.5 Hz), 11.68(1H, brs)

7-(2-Naphtyl)quinoline-4(1H)-thione (Compound 46)

Melting Point: 160°–165° C. (dec.); MS m/z: 287 (M$^+$); NMR(DMSO-d$_6$)δ: 7.31(1H, d, J=6.0 Hz), 7.57–7.62(2H, m), 7.87–8.10(7H, m), 8.35(1H, s), 8.80(1H, d, J=8.6 Hz), 12.91(1H, brs)

7-Benzylquinoline-4(1H)-thione (Compound 47)

Melting Point: 155°–157° C. (dec.); MS m/z: 251 (M$^+$); NMR(DMSO-d$_6$)δ: 4.10(2H, s), 7.20–7.36(7H, m), 7.41 (1H, s), 7.77(1H, d, J=6.3 Hz), 8.60(1H, d, J=8.6 Hz), 12.77(1H, brs)

7-N,N-Dimethylaminoquinoline-4(1H)-thione (Compound 48)

Melting Point: 219.0°–221.0° C.; MS m/z: 204 (M$^+$); NMR(DMSO-d$_6$)δ: 3.05(6H, s), 6.52(1H, d, J=2.3 Hz), 6.96(1H, d, J=6.9 Hz), 7.04(1H, dd, J=2.3, 9.2 Hz), 7.59(1H, dd, J=6.3, 6.9 Hz), 8.46(1H, d, J=9.5 Hz), 12.27(1H, brs)

7-Isopropylthioquinoline-4(1H)-thione (Compound 49)

Melting Point: 170.0° C. (dec.); MS m/z: 235 (M$^+$); NMR(DMSO-d$_6$)δ: 1.35(6H, d, J=6.6 Hz), 3.70(1H, sept, J=6.6 Hz), 7.21(1H, d, J=6.6 Hz), 7.37(1H, dd, J=2.0, 8.6 Hz), 7.50(1H, d, J=2.0 Hz), 7.80(1H, t, J=6.3 Hz), 8.56(1H, d, J=8.6 Hz), 12.72(1H, brs)

7-(2-Benzimidazolyl)thiomethylquinoline-4(1H)-thione (Compound 50)

Melting Point: >145° C. (dec.); FAB-MS m/z: 324 [M+H]$^+$; NMR(DMSO-d$_6$)δ: 4.77(2H, s), 7.10–7.20(2H, m), 7.25(1H, d, J=6.3 Hz), 7.40(2H, br), 7.54(1H, dd, J=1.7, 8.6 Hz), 7.72(1H, d, J=1.7 Hz), 7.78(1H, t, J=6.3 Hz), 8.60(1H, d, J=8.6 Hz), 12.60(1H, brs), 12.85(1H, brs)

Example 3:

7-Nitroquinoline-4(1H)-thione (Compound 19)

4-Chloro-7-nitroquinoline (100 mg, 0.48 mmol) and thiourea (100 mg, 1.3 mmol) were added to ethanol (50 ml) and stirred at 80° C. for 30 minutes. After allowing to cool to room temperature, ethanol was removed under reduced pressure. The residue was chromatographed by silica gel column chromatography and eluted with mixed solution of methylene chloride with methanol (19 : 1) for collection of yellow bands. The solvent was removed to obtain 7 mg (7%) of the titled yellow compound.

Melting Point: >250° C.; MS m/z: 206 (M$^+$); NMR (CD$_3$OD)δ: 7.45(1H, d, J=6.9 Hz), 7.73(1H, d, J=6.9 Hz), 8.08(1H, dd, J=2.3, 9.2 Hz), 8.39(1H, d, J=2.3 Hz), 8.87(1H, d, J=9.2 Hz)

Example 4:

7-Ethoxyquinoline-4(1H)-thione (Compound 22)

4-Chloro(bromo)-7-ethoxyquinoline (180 mg) and 70% sodium hydrosulfide (250 mg) were dissolved in methanol (50 ml) and refluxed for 15 hours. This reaction mixture was evaporated under reduced pressure and the residue was developed by silica gel column chromatography [Wako Gel™ C-200, mixed solution of methylene chloride with methanol (9 : 1)]. Fractions corresponding to yellow spots were collected and evaporated to obtain crude crystals. The obtained crude crystals were recrystallized from 40% aqueous ethanol solution to obtain 107 mg of the titled compound. Melting Point: 171°–174° C.; MS m/z: 205 (M$^+$); NMR(DMSO-d$_6$)δ: 1.40(3H, t, J=6.9 Hz), 4.15(2H, q, J=6.9 Hz), 7.02(1H, d, J=1.3 Hz), 7.09(1H, dd, J=2.3, 9.2 Hz), 7.15(1H, d, J=6.5 Hz), 7.73–7.78(1H, m), 8.58(1H, d, J=9.2 Hz), 12.68(1H, brs)

In accordance with the procedure of the Example 4, the following compounds were obtained from corresponding starting materials.

7-Isopropyloxyquinoline-4(1H)-thione (Compound 23)

Melting Point: 174°–176° C.; MS m/z: 219 (M$^+$); NMR (DMSO-d$_6$)δ: 1.42(6H, d, J=5.9 Hz), 4.80(1H, sept, J=5.9 Hz), 7.08(1H, d, J=2.3 Hz), 7.15(1H, dd, J=2.3, 9.2 Hz), 7.21(1H, d, J=6.3 Hz), 7.83(1H, dd, J=6.3, 6.6 Hz), 8.64(1H, d, J=9.2 Hz), 12.67(1H, brs)

7-n-Hexyloxyquinoline-4(1H)-thione (Compound 24)

Melting Point: 153°–156° C.; MS m/z: 261 (M$^+$); NMR (DMSO-d$_6$)δ: 0.91(3H, t, J=6.6 Hz), 1.31–1.49(6H, m), 1.80(2H, quint, J=6.6 Hz), 4.10(2H, t, J=6.6 Hz), 7.02(1H, d, J=2.3 Hz), 7.10(1H, dd, J=2.3, 9.2 Hz), 7.16(1H, d, J=6.3 Hz), 7.77(1H, dd, J=6.3, 6.6 Hz), 8.59(1H, d, J=9.2 Hz), 12.63(1H, brs)

7-Benzyloxyquinoline-4(1H)-thione (Compound 25)

Melting Point: 166°–170° C.; MS m/z: 267 (M⁺); NMR (DMSO-d₆)δ: 5.33(2H, s), 7.18–7.28(3H, m), 7.41-7.60(5H, m), 7.84(1H, dd, J=5.9, 6.6 Hz), 8.68(1H, d, J=9.2 Hz), 12.76(1H, brs)

7-n-Propoxyquinoline-4(1H)-thione (Compound 26)

Melting Point: 178°–182° C.; MS m/z: 219 (M⁺); NMR (DMSO-d₆)δ: 1.10(3H, t, J=7.3 Hz), 1.92(2H, sext, J=7.3 Hz), 4.13(2H, t, J=6.6 Hz), 7.09(1H, d, J=2.3 Hz), 7.18(1H, dd, J=2.3, 9.2 Hz), 7.23(1H, d, J=2.3 Hz), 7.80(1H, dd, J=6.3, 6.6 Hz), 8.66(1H, d, J=9.2 Hz), 12.71(1H, brs)

7-Hydroxyquinoline-4(1H)-thione (Compound 27)

Melting Point: 245°–255° C. (dec.); MS m/z: 177 (M⁺); NMR(DMSO-d₆)δ: 6.99(1H, d, J=2.0 Hz), 7.04(1H, dd, J=2.3, 9.2 Hz), 7.17(1H, d, J=6.6 Hz), 7.78(1H, d, J=6.6 Hz), 8.61(1H, d, J=9.2 Hz), 10.64(1H, s), 12.63(1H, brs)

7-Methanesulfonyloxyquinoline-4(1H)-thione (Compound 28)

Melting Point: 185°–188° C.; MS m/z: 255 (M⁺); NMR (DMSO-d₆)δ: 3.59(3H, s), 7.39(1H, d, J=6.6 Hz), 7.52(1H, dd, J=2.3, 9.2 Hz), 7.73(1H, d, J=2.3 Hz), 7.99(1H, dd, J=6.6, 6.3 Hz), 8.83(1H, d, J=9.2 Hz), 13.05(1H, brs)

7-Dodecyloxyquinoline-4(1H)-thione (Compound 52)

Melting Point: 141°–145° C.; MS m/z: 345 (M⁺); NMR (DMSO-d₆)δ: 0.85(3H, t, J=6.6 Hz), 1.24–1.44(18H, m), 1.72–1.82(2H, m), 4.08(2H, t, J=6.6 Hz), 6.99(1H, d, J=2.3 Hz), 7.07(1H, dd, J=2.3, 9.2 Hz), 7.14(1H, d, J=6.6 Hz), 7.75(1H, t, J=6.6 Hz), 8.58(1H, d, J=9.2 Hz), 12.60(1H, brs)

7-Octyloxyquinoline-4(1H)-thione (Compound 53)

Melting Point: 150°–154° C.; MS m/z: 289 (M⁺); NMR (DMSO-d₆)δ: 0.87(3H, t, J=6.6 Hz), 1.27-1.44(1OH, m), 1.73–1.83(2H, m), 4.08(2H, t, J=6.6 Hz), 7.00(1H, d, J=2.3 Hz), 7.07(1H, dd, J=2.3, 9.2 Hz), 7.15(1H, d, J=6.6 Hz), 7.75(1H, t, J=6.6 Hz), 8.58(1H, d, J=9.2 Hz), 12.60(1H, brs)

7-(5-Carboxy-n-pentyloxy)quinoline-4(1H)-thione (Compound 51)

Melting Point: 186°–190° C.; FAB-MS m/z: 292 [M+H]⁺; NMR(DMSO-d₆)δ: 1.40–1.85(6H, m), 2.25(2H, t, J=6.9 Hz), 4.08(2H, t, J=6.6 Hz), 7.00(1H, d, J=2.3 Hz), 7.06(1H, dd, J=2.3, 9.2 Hz), 7.15(1H, d, J=6.6 Hz), 7.74(1H, m), 8.58(1H, d, J=9.2 Hz), 11.98(1H, brs), 12.61(1H, brs)

Example 5:

7-Acetoxymethylquinoline-4(1H)-thione (Compound 29)

7-Hydroxymethylquinoline-4(1H)-thione(60 mg, 0.3 mmol) obtained in the Example 2 was dissolved in acetic anhydride (5 ml). The mixture was added with pyridine (23.5 mg, 0.3 mmol) and stirred at room temperature for 24 hours. Excess water was added under cooling to the reaction mixture for decomposition of acetic anhydride into homogeneous solution. Then, the solution was adjusted by 2N aqueous solution of sodium hydroxide to pH 5.5 and the resulting precipitates were filtered off. The filtrate was further adjusted by saturated aqueous solution of potassium carbonate to pH 8–9. Then, the filtrate was extracted with ethyl acetate (20 ml×3), and the combined extract solutions were washed with water and dried over magnesium sulfate. The solvent was removed under reduced pressure and the residue was sufficiently washed with ether to obtain 34 mg (46%) of the titled orange compound.

Melting Point: 153°–156° C.; MS m/z: 233 (M⁺); NMR (DMSO-d₆)δ: 2.13(3H, s), 5.24(2H, s), 7.28(1H, d, J=6.6 Hz), 7.43(1H, dd, J=1.3, 8.6 Hz), 7.62(1H, s), 7.83(1H, m), 8.65(1H, d, J=8.6 Hz), 12.89(1H, brs)

Example 6:

7-(1-Piperazinyl)quinoline-4(1H)-thione (Compound 54)

4-Hydroxy-7-(4-methoxycarbonyl-1-piperazinyl) quinoline (0.32 g, 1.1 mmol) dissolved in methanol (5 ml) was added with 2N sodium hydroxide (1.6 ml) and stirred with heating for 12 hours. After allowing to cool, methanol was removed under reduced pressure. The residue was added with water (10 ml) and adjusted by 5% hydrochloric acid to pH 7 and the water was removed under reduced pressure. This residue was siispended in pyridine (5 ml), added with phosphorus pentasulfide (0.25 g, 1.1 mmol) and stirred at 100° C. for 1.5 hours. After allowing to cool, pyridine was removed under reduced pressure and the residue was purified by preparative TLC (Merck Art. 13895, methylene chloride : methanol : ammonia water=50 : 10 : 1) to obtain 21 mg (8%) of the titled compound.

Melting Point: 220°–225° C. (dec.); MS m/z: 245 (M⁺); NMR(DMSO-d₆)δ: 3.24(4H, brs), 3.56(4H, brs), 6.94(1H, brs), 7.07(1H, d, J=6.4 Hz), 7.27(1H, d, J=9.4 Hz), 7.67(1H, d, J=6.4 Hz), 8.51(1H, d, J=9.4 Hz), 9.30(1H, brs)

Example 7:

Sodium salt of 7-(5-carboxy-n-pentyloxy)quinoline-4(1H)-thione 7-(5-Carboxy-n-pentyloxy)quinoline-4(1H)-thione (43.7 mg, 0.15 mmol) and sodium carbonate (7.9 mg, 0.075 mmol) were stirred in water (50 ml) overnight and freeze-dried to obtain 43.2 mg (92%) of the titled compound.

Melting Point: 231°–235° C.; NMR(DMSO-d₆)δ: 1.4–1.8 (6H, m), 2.09(2H, t, J=6.9 Hz), 4.01(2H, t, J=6.6 Hz), 6.87(1H, dd, J=2.3, 9.3 Hz), 7.03(1H, d, J=2.3 Hz), 7.33(1H, d, J=5.3 Hz), 7.80(1H, d, J=5.3 Hz), 8.59(1H, d, J=9.2 Hz)

Capability Of Exploitation In Industry

The compound according to the present invention has excellent selective antibacterial activity against *Helicobacter pylori* and therefore is effective for treatment and prevention of reccurrence of peptic ulcers and chronic gastritis with *Helicobacter pylori* infections.

We claim:

1. A thioquinolone compound represented by the formula I or pharmaceutically acceptable salt thereof:

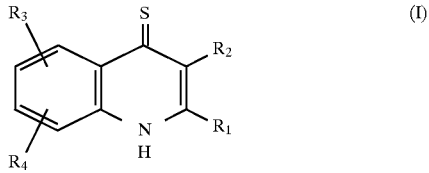

wherein $R_1$ and $R_2$ respectively represent hydrogen atom or $R_1$ and $R_2$ are joined to form —O—$(CH_2)_2$—;

$R_3$ represents halogen atom, $C_1$–$C_{12}$ alkyl group, $C_1$–$C_{12}$ alkoxy group, lower alkylsulfonyloxy group, carboxy lower alkoxy group, lower alkylthio group, benzyloxy group, benzylthio group, phenoxy group, styryl group, nitro group, phenyl group, naphthyl group, piperazinyl group, morpholino group or hydroxyl group or represents —$CH_2R_5$, —$COR_6$ or —$NR_7R_8$ wherein $R_5$ represents benzyl group, phenyl group, hydroxyl group, lower alkoxy group, lower alkylcarbonyloxy group, phenoxy group, di-lower alkylamino group or benzimidazolylthio group, $R_6$ represents lower alkyl group or amino group and $R_7$ and $R_8$ respectively represent lower alkyl group; and $R_4$ represents hydrogen atom or lower alkyl group or is coupled with $R_3$ to form cyclohexene ring, benzene ring or pyridine ring, $R_3$ being not halogen atom at any of positions 5 to 8, methyl group at position 6 or methoxy group at position 6 of the quiinoline ring when $R_1$, $R_2$ and $R_4$ are respectively hydrogen atom, $R_3$ and $R_4$ being not at positions 6 and 7 or positions 6 and 8 of the quinoline ring when $R_1$ and $R_2$ are respectively hydrogen atom and $R_4$ is lower alkyl group.

2. The compound according to claim 1 wherein $R_1$, $R_2$ and $R_4$ are respectively hydrogen atom.

3. The compound according to claim 1 wherein $R_1$, $R_2$ and $R_4$ are respectively hydrogen atom and $R_3$ is at position 7 of the quinoline ring.

4. The compound according to claim 3 wherein $R_3$ is $C_1$–$C_{12}$ alkyl group, $C_1$–$C_{12}$ alkoxy group, benzyl group, phenethyl group, lower alkoxymethyl group, lower alkylcarbonyloxymethyl group, phenoxymethyl group, styryl group, phenyl group, phenoxy group, carboxy-lower alkoxy group, lower alkylsulfonyloxy group, lower alkylthio group, benzylthio group, di-lower alkylamino group, piperazinyl group, morpholino group or benzimidazolylthiomethyl group.

5. The compound according to claim 1 wherein $R_1$, $R_2$ and $R_4$ are respectively hydrogen atom and $R_3$ is at position 8 of the quinoline ring.

6. The compound according to claim 5 wherein $R_3$ is lower alkyl group or lower alkoxy group.

7. The compound according to claim 1 wherein $R_1$ and $R_2$ are respectively hydrogen atom and $R_3$ and $R_4$ are at positions 7 and 8 of the quinoline ring.

8. The compound according to claim 7 wherein $R_3$ and $R_4$ are respectively lower alkyl group.

9. The compound according to claim 7 wherein $R_3$ and $R_4$ are joined to form cyclohexene ring or benzene ring.

10. A pharmaceutical composition containing an effective amount of compound according to any one of claims 1 to 9 and a pharmaceutically acceptable diluent or carrier.

11. The compound according to claim 1, wherein $R_3$ represents halogen atom, $C_1$–$C_{12}$ alkyl group, $C_1$–$C_{12}$ alkoxy group, lower alkylsulfonyloxy group, carboxy lower alkoxy group, lower alkylthio group, benzyloxy group, benzylthio group, phenoxy group, styryl group, nitro group, phenyl group, naphthyl group, morpholino group or hydroxyl group or represents —$CH_2R_5$, —$COR_6$ or —$NR_7R_8$ wherein $R_5$ represents benzyl group, phenyl group, hydroxyl group, lower alkoxy group, lower alkylcarbonyloxy group, phenoxy group, di-lower alkylamino group or benzimidazolylthio group, $R_6$ represents lower alkyl group or amino group and $R_7$ and $R_8$ respectively represent lower alkyl group.

12. An antibacterial agent effective against Helicobacter, wherein the agent comprises the compound according to claim 1.

13. The antibacterial agent according to claim 12, wherein the agent is effective against *Helicobacter pylori*.

14. A method of inhibiting the growth of cells of Helicobacter comprising the step of contacting the cells with an effective amount of a thioquinolone compound represented by the formula I or pharmaceutically acceptable salt thereof:

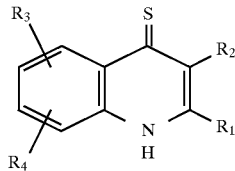

wherein $R_1$ and $R_2$ respectively represent hydrogen atom or $R_1$ and $R_2$ are joined to form —O—$(CH_2)_2$—;

$R_3$ represents halogen atom, $C_1$–$C_{,2}$ alkyl group, $C_1$–$C_{12}$ alkoxy group, lower alkylsulfonyloxy group, carboxy lower alkoxy group, lower alkylthio group, benzyloxy group, benzylthio group, phenoxy group, styryl group, nitro group, phenyl group, naphthyl group, piperazinyl group, morpholino group or hydroxyl group or represents —$CH_2R_5$, —$COR_6$ or —$NR_7R$, wherein $R_5$ represents benzyl group, phenyl group, hydroxyl group, lower alkoxy group, lower alkylcarbonyloxy group, phenoxy group, di-lower alkylamino group or benzimidazolylthio group, $R_6$ represents lower alkyl group or amino group and $R_7$ and $R_8$ respectively represent lower alkyl group; and $R_4$ represents hydrogen atom or lower alkyl group or is coupled with $R_3$ to form cyclohexene ring, benzene ring or pyridine ring, $R_3$ being not halogen atom at any of positions 5 to 8, methyl group at position 6 or methoxy group at position 6 of the quinoline ring when $R_1$, $R_2$ and $R_4$ are respectively hydrogen atom, $R_3$ and $R_4$ being not at positions 6 and 7 or positions 6 and 8 of the quinoline ring when $R_1$ and $R_2$ are respectively hydrogen atom and $R_4$ is lower alkyl group.

15. The method according to claim 14, wherein the cells are cells of *Helicobacter pylori*.

16. A method of treating peptic ulcer or chronic gastritis comprising the step of administering to a patient in need thereof an effective amount of a thioquinolone compound represented by the formula I or pharmaceutically acceptable salt thereof:

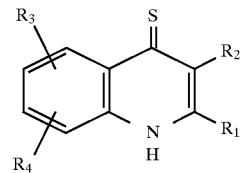

wherein $R_1$ and $R_2$ respectively represent hydrogen atom or $R$ and $R_2$ are joined to form —O—$(CH_2)_2$—;

$R_3$ represent halogen atom, $C_1$–$C_{12}$ alkyl group, $C_1$–$C_{12}$ alkoxy group, lower alkylsulfonyloxy group, carboxy lower alkoxy group, lower alkylthio group, benzyloxy group, benzylthio group, phenoxy group, styryl group, nitro group, phenyl group, naphthyl group, piperazinyl group, morpholino group or hydroxyl group or represents —$CH_2R_5$, —$COR_6$ or —$NR_7R_5$ wherein $R_5$ represents benzyl group, phenyl group, hydroxyl group, lower alkoxy group, lower alkylcarbonyloxy group, phenoxy group, di-lower alkylamino group or benzimidazolylthio group, $R_6$ represents lower alkyl group or amino group and $R_7$ and $R_8$ respectively represent lower alkyl group; and $R_4$ represents hydrogen atom or lower alkyl group or is coupled with $R_3$ to form cyclohexene ring, benzene ring or pyridine ring, $R_3$ being not halogen atom at any of positions 5 to 8, methyl group at position 6 or methoxy group at position 6 of the quinoline ring when $R_1$, $R_2$ and $R_4$ are respectively hydrogen atom, $R_3$ and $R_4$ being not at positions 6 and 7 or positions 6 and 8 of the quinoline ring when $R_1$ and $R_2$ are respectively hydrogen atom and $R_4$ is lower alkyl group.

17. The method according to claim 16, wherein the compound is administered orally or parenterally.

18. The method according to claim 17, wherein, if the compound is administered orally, the compound is administered in the form of a tablet, powder, granule, capsule, microcapsule, or syrup.

19. The method according to claim 17, wherein, if the compound is administered parenterally, the compound is administered in the form of an injection.

20. The method according to claim 19, wherein the compound is in freeze-dried form or in the form of a suppository.

* * * * *

UNITED STATES PATENT AND TRADEMARK OFFICE
CERTIFICATE OF CORRECTION

PATENT NO. : 5,773,449
DATED : June 30, 1998
INVENTOR(S) : Masataka KONISHI, et al.

It is certified that error appears in the above-identified patent and that said Letters Patent is hereby corrected as shown below:

Column 1, line 5, "PCT/JP95102052" should read
--PCT/JP95/02052--.

Column 4, line 40, "p-toluenesulfonate salicylate" should read
--p-toluenesulfonate and salicylate--.

Column 7, line 26, "and-negative" should read and -negative--;
line 45, "1.0x106CFU/ml" should read --
1.0x10$^6$CFU/ml--.

Column 12, line 47, "4-Hydroxy-, 10-phenanthroline" should
read --4-Hydroxy-1, 10-phenanthroline--.

Column 19, line 25, "J=8.6" should read --J=8.6Hz--.

Column 22, line 5, "siispended" should read --suspended--.

Column 23, line 66, "-NR$_7$R," should read --NR$_7$R$_8$--.

UNITED STATES PATENT AND TRADEMARK OFFICE
CERTIFICATE OF CORRECTION

PATENT NO. : 5,773,449
DATED : June 30, 1998
INVENTOR(S) : Masataka KONISHI, et al.

It is certified that error appears in the above-identified patent and that said Letters Patent is hereby corrected as shown below:

Column 24, line 31, "Rand $R_2$" should read --$R_1$ and $R_2$--.

Signed and Sealed this

Fifteenth Day of June, 1999

Attest:

Q. TODD DICKINSON

Attesting Officer — Acting Commissioner of Patents and Trademarks